United States Patent [19]
Chutkow et al.

[11] Patent Number: 5,551,446
[45] Date of Patent: Sep. 3, 1996

[54] REFLEX MEASURING DEVICE, AND METHOD

[75] Inventors: Jerry G. Chutkow, Clarence, N.Y.; Patrick Flanagan, North Royalton, Ohio; Michael T. Riggs, Batavia, N.Y.

[73] Assignee: Apollo Research Corp., Lancaster, N.Y.

[21] Appl. No.: 256,381

[22] PCT Filed: Dec. 30, 1992

[86] PCT No.: PCT/US92/11284

§ 371 Date: Jul. 8, 1994

§ 102(e) Date: Jul. 8, 1994

[87] PCT Pub. No.: WO94/15540

PCT Pub. Date: Jul. 21, 1994

[51] Int. Cl.$^6$ .................................................. A61B 5/00
[52] U.S. Cl. ........................................ 128/782; 128/749
[58] Field of Search .................................. 128/740, 741, 128/774, 782; 369/413.01, 413.02; 73/12

[56] References Cited

U.S. PATENT DOCUMENTS

| | | | |
|---|---|---|---|
| 2,685,286 | 8/1954 | Torricelli | 128/740 |
| 2,716,978 | 9/1955 | Torricelli | 128/740 |
| 2,744,520 | 5/1956 | Torricelli | 128/740 |
| 2,800,895 | 7/1957 | Torricelli | 128/740 |
| 3,626,927 | 12/1971 | Breneman | 128/740 |
| 4,682,490 | 7/1987 | Adelman et al. | 73/12 |
| 5,012,820 | 5/1991 | Meyer | 128/741 X |
| 5,195,532 | 3/1993 | Schumacher et al. | 128/740 X |

*Primary Examiner*—Sam Rimell
*Attorney, Agent, or Firm*—Phillips, Lytle, Hitchcock, Blaine & Huber

[57] ABSTRACT

An improved reflex gun (21) is adapted to measure certain parameters of a stimulus supplied to a tendon, and the patient's response thereto. The gun has a trigger (29) which, when squeezed, supplies a signal to a computer (24). The computer then causes a waveform generator (32) to provide current pulses of desired magnitude, shape and duration to a solenoid (50) in the gun. Such energization of the solenoid coil, causes a plunger (52) to impact against one end of a force sensor (22). The other end of the force sensor is held against the patient's skin with a preload force sufficient to measure the patient's response to a force stimulus. The force sensor has a transducer (132) for measuring the certain parameters of the impact force and the patient's response. The improved device may be used to determine quantitatively certain parameters of the stimulus and response, and provides a diagnostic tool for a physician.

15 Claims, 6 Drawing Sheets

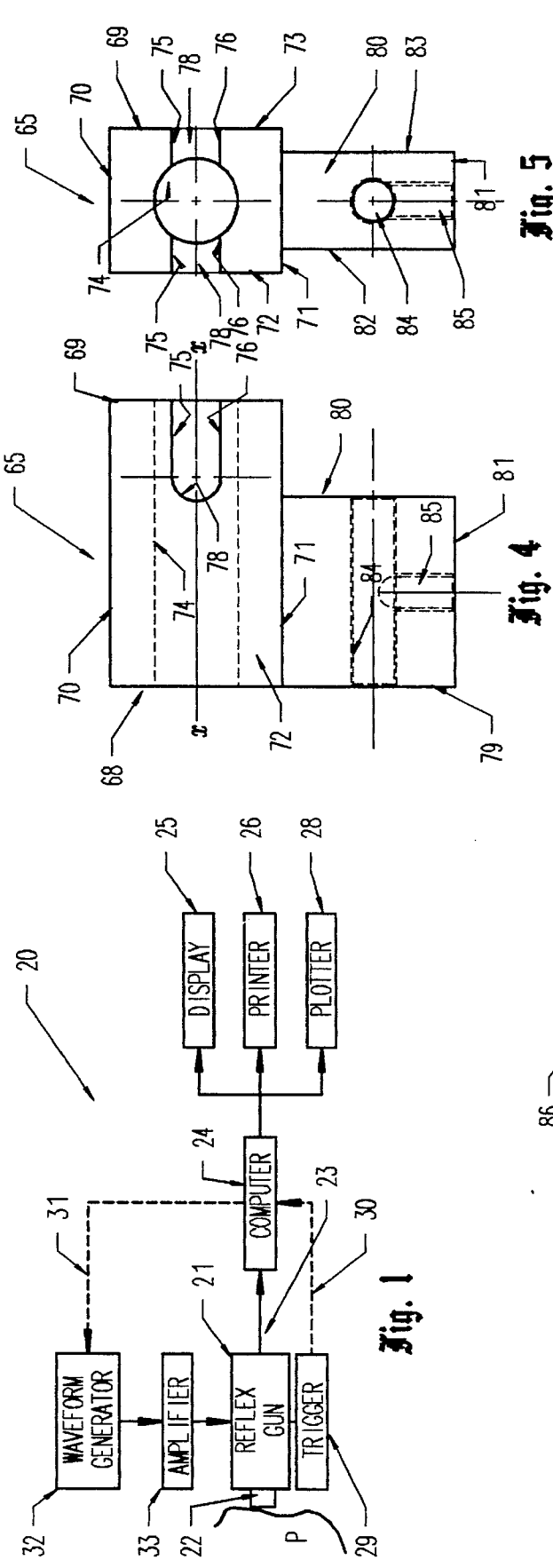
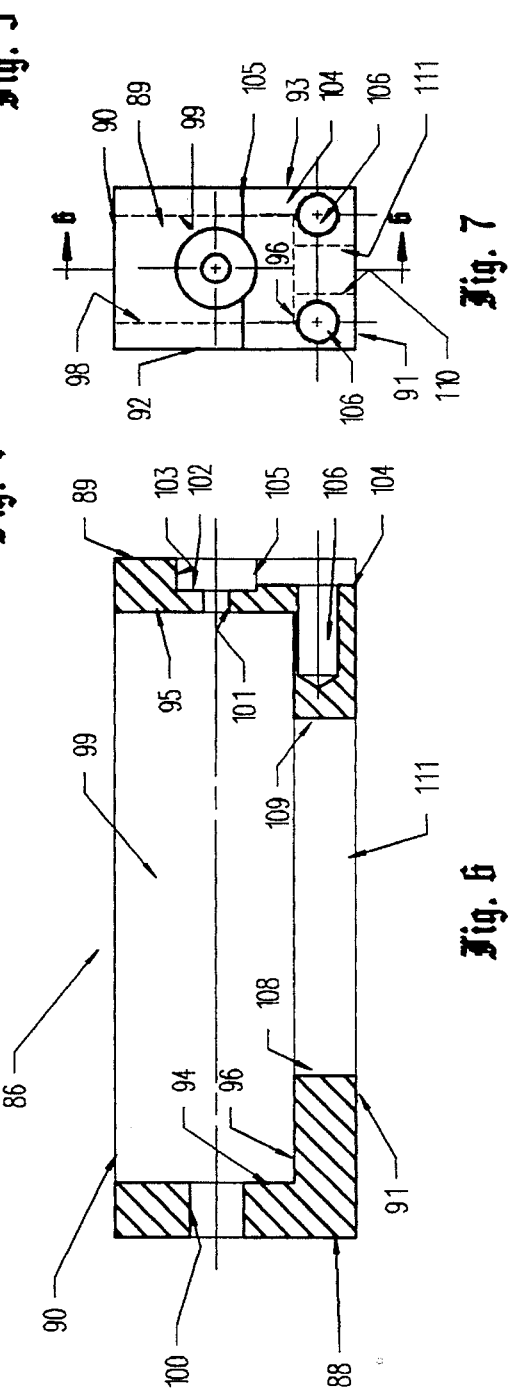

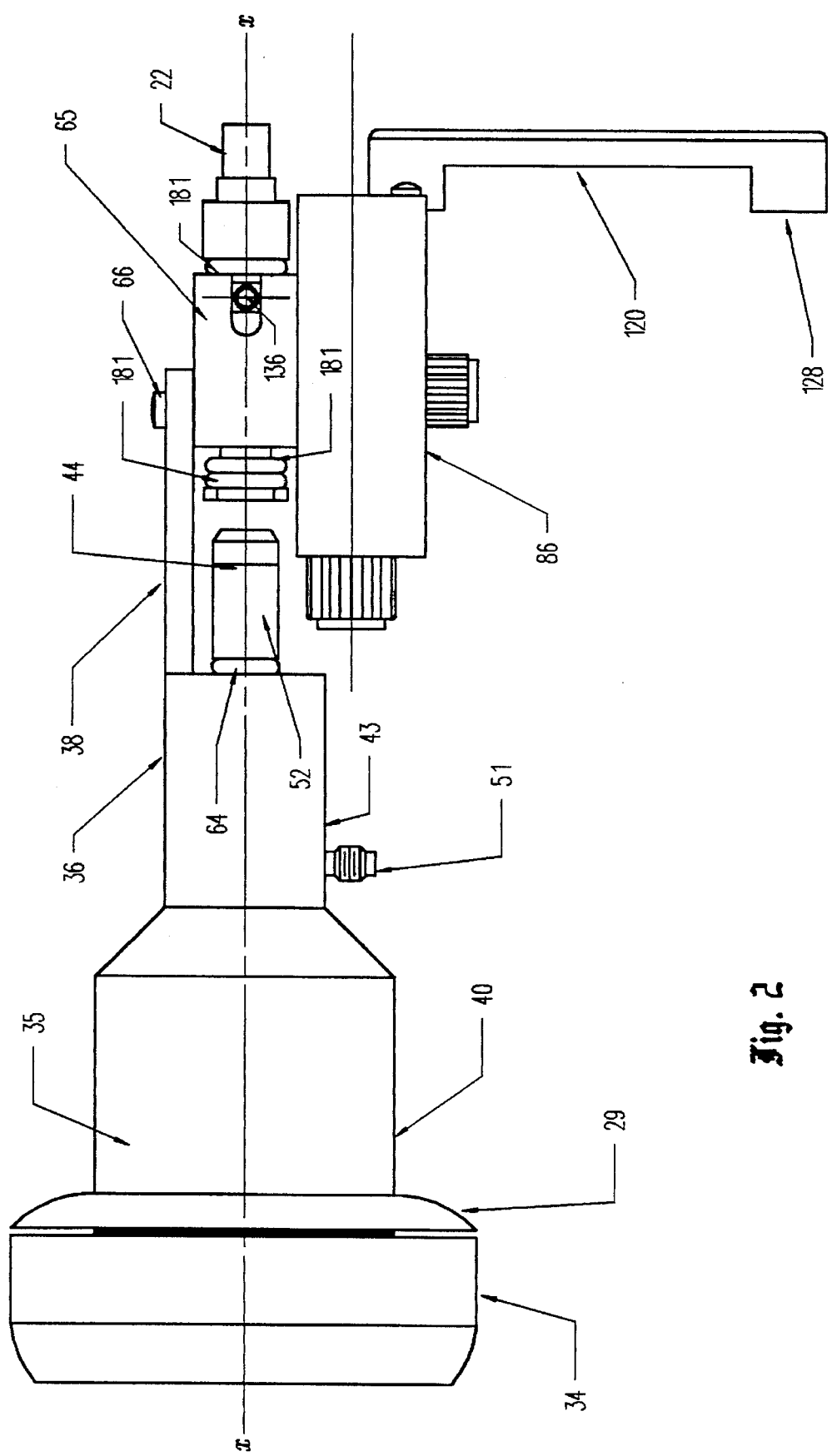

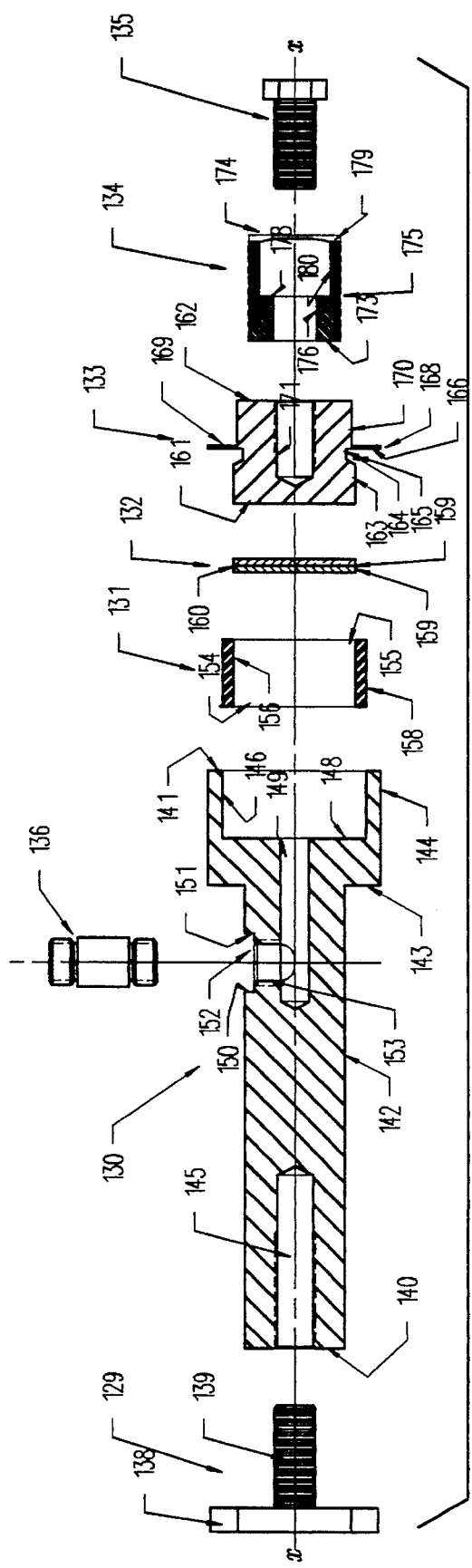
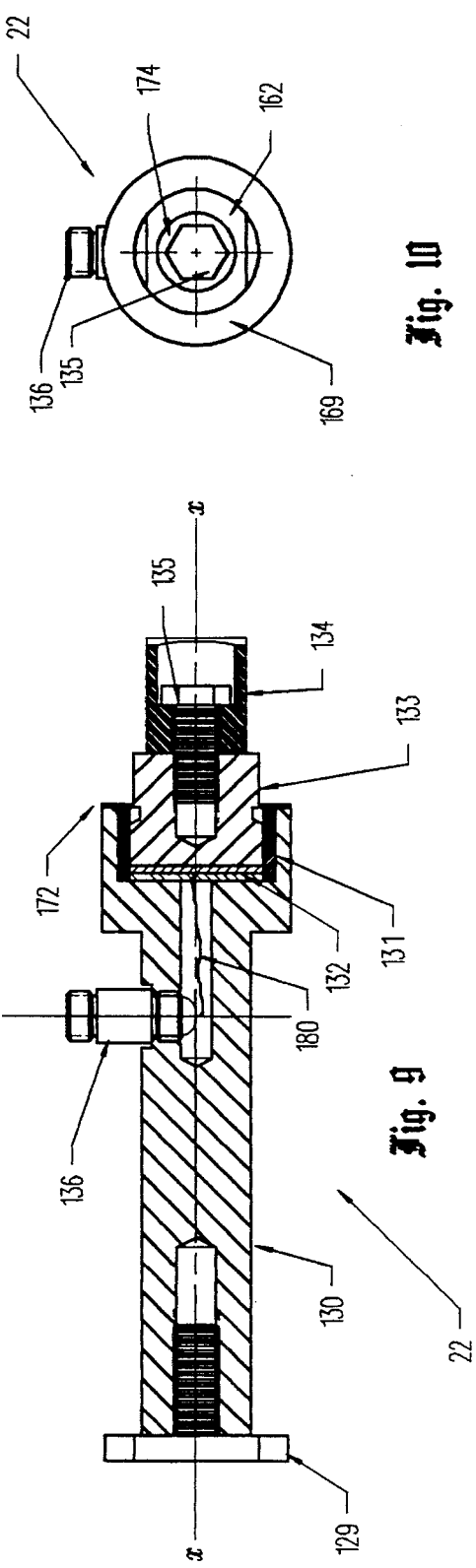
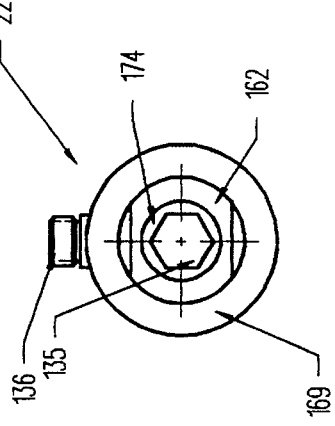
Fig. 8
Fig. 9
Fig. 10

REFLEX MEASURING DEVICE, AND METHOD

TECHNICAL FIELD

The present invention relates generally to reflex measuring devices and methods for determining the physical reflex response of a patient to a supplied stimulus, and, more particularly, to an improved method and apparatus for sensing and measuring quantitatively certain parameters of the patient's response to such a stimulus.

BACKGROUND ART

Physicians commonly attempt to determine the existence vel non of a patient's muscular response to an applied stimulus, by means of a rubber hammer. Basically, the physician taps a tendon through the skin, and then looks for an involuntary physical response. For example, to test the reaction of the quadricep muscle, the physician will typically ask the patient to first cross his legs while sitting on an examination table. The physician will then tap the quadricep tendon beneath the skin in the vicinity of the knee, and will then look for an involuntary knee-jerk reaction. Upon information and belief, such impulse tapping of this tendon causes the quadricep muscle to contract, causing the involuntary knee-jerk reaction. This technique is also generally used to test the muscular response to a stimulus applied to the achilles tendon, the bicep tendon, the tricep tendon, the brachii radialis, the hamstrings, and the jaw tendons.

Upon information and belief, some physicians have physically placed their finger(s) against the tendon, and have tapped their fingers with the tap hammer. Thus, the impact force transmitted from the hammer to the finger(s) is transmitted through the fingers and the patient's skin to the tendon itself. This technique is believed to permit the physician to "feel" the patient's response, rather than to rely solely on visual observation. In either case, the use of such data has heretofore been limited, and is necessarily subjective. Such data is usually limited to determining whether the patient exhibits a response, or not.

After the stimulus has been applied (i.e., the tendon has been tapped), the impact stimulus must be transmitted along various afferent (sensory) nerves to the spinal cord, must traverse at least one electrochemical synapse to excite the cell bodies of the motor neurons in the cord and to transmit the resulting action potentials from the cord to the muscle membranes along efferent (motor) fibers, must cross the electrochemical neuromuscular junction, and must conduct the resulting action potentials along the muscle membranes to the myofibrils where mechanical contraction occurs. Anything (e.g., disease, injury, etc.) that slows the transmission of neurological conductivity along the foregoing path, will delay the onset of the patient's physical response to the stimulus. This delay is known as "latency". Moreover, the magnitude of the response, or at least the ratio of the response force to the stimulus force, is an indication of the capacity of the conductive path.

Accordingly, it would be generally desirable to quantify and record the data performed by such testing. Such testing is non-invasive, inexpensive and may readily be performed in the physician's office. Moreover, such quantitative data of the parameters of such response (e.g., the period of latency, the response-to-stimulus amplitude ratio, etc.) from tests taken at different times, may possibly be compared to indicate the effectiveness of therapy, or of healing of damaged nerves and tissue. Thus, there is believed to be a definite need for a device for measuring, quantifying and recording certain parameters of such reflex response testing.

DISCLOSURE OF THE INVENTION

The present invention provides an improved method and apparatus for measuring, quantifying and recording certain parameters of a patient's physical response to application of an external stimulus.

With parenthetical reference to the corresponding parts, portions or surfaces of the disclosed embodiment for exemplary purposes only, the improved device (e.g., 21) broadly includes: stimulus means (e.g., 50,52) for selectively applying a stimulus (e.g., force, noise, light, etc.) to a patient; and sensor means (e.g., 22) for sensing and measuring certain parameters (e.g. latency of response, amplitude of response, response-to-stimulus ratio, etc.) of the patient's physical response to the stimulus.

The sensor means has a body member (e.g., 130) and a head (e.g., 133) mounted for movement relatively toward and away from one another, and has a transducer (e.g., 132) operatively arranged between the body member and head. The head has a surface (e.g., 174) adapted to continuously bear against a portion of the patient's body during the time period between application of the stimulus and the end of the measurement of the patient's response thereto. In the preferred embodiment, the stimulus is applied to the body through the sensor means, although this is not invariable. The sensor means is operatively arranged to sense and quantitatively measure certain parameters of the patient's response to the stimulus, as a function of the output signal of the transducer. Such output signal may be supplied to a computer, and the results of such testing may be calculated, computed or otherwise manipulated, displayed on a video screen and/or preserved as hard copy via the output of an associated printer or plotter.

In another aspect, the invention provides an improved method for measuring such parameters of a patient's physical response to application of an external stimulus, which method comprises the steps of: causing a sensor to continuously bear against a portion of a patient's body during the time period between application of the stimulus and the end of the measurement of the patient's response, the sensor having a member and head mounted for relative movement toward and away from one another and having a transducer operatively arranged therebetween, the transducer being arranged to measure the relative displacement between the member and head; selectively applying a stimulus to the patient; and sensing and measuring certain parameters of the patient's physical response to the stimulus as a function of the output signal of the transducer. The improved method preferably includes the steps of displaying and/or recording the data generated by the sensor. Thus, data from tests conducted at different times may be compared, and such comparison may be interpreted by the physician to assess the patient's response to medication or general healing as a function of time.

Accordingly, the general object of this invention is to provide improved apparatus for sensing and measuring quantitatively certain parameters of a patient's physical response to application of an external stimulus.

Another object is to provide an improved method for recording certain parameters of a patient's reflex response to an external stimulus.

These and other objects and advantages will become apparent from the foregoing and ongoing written specification, the drawings, and the appended claims.

BRIEF DESCRIPTION OF THE DRAWINGS

FIG. 1 is a block diagram showing the improved reflex-measuring gun or stimulator as being operatively associated with a computer arranged to provide an output to a display, a printer and/or a plotter, and further illustrating a manually-operable trigger on the gun arranged to provide an appropriate signal through the computer for causing the device to apply a force stimulus to the patient.

FIG. 2 is a side elevation of the improved reflex measuring gun.

FIG. 4 is a front elevation of the L-shaped frame member in which the force sensor is slidably mounted.

FIG. 5 is a right end elevation of the frame member shown in FIG. 4.

FIG. 6 is a fragmentary vertical sectional view of the frame slide member, this view being taken generally on line 6—6 of FIG. 7.

FIG. 7 is a right end elevation of the slide member shown in FIG. 6.

FIG. 8 is a longitudinal view, partly in elevation and partly in vertical cross-section, showing the various parts and components of the force sensor in exploded aligned relation.

FIG. 9 is a longitudinal view, again partly in elevation and partly in vertical section, of the assembled force sensor shown in FIG. 8.

FIG. 10 is a right end elevation of the force sensor shown in FIG. 9.

MODE(s) OF CARRYING OUT IN THE INVENTION

Figure 3:
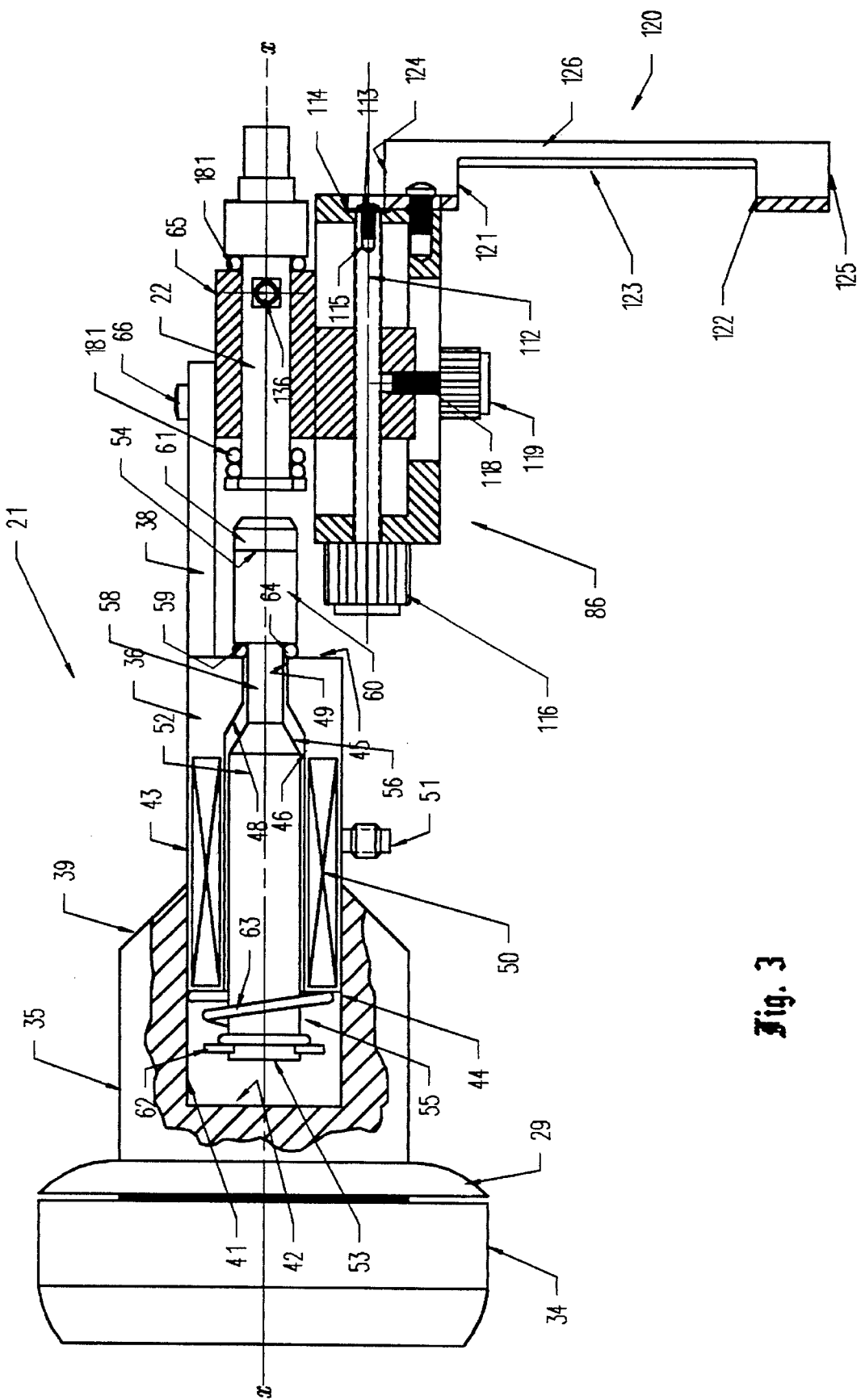
FIG. 3 is a longitudinal view, partly in section and partly in elevation, of the device shown in FIG. 2, showing the stimulus-applying solenoid, the sensor, and the frame.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

This invention provides an improved reflex measuring device, and method of operating same, for sensing and measuring certain (i.e., some, but not necessarily all) parameters of a patient's physical response to application of an external stimulus. As used herein, the term "patient" refers to mammals generally, and is not specifically limited to human beings. Hence, the term "patient" specifically includes animals. Moreover, while the invention will not be described in terms of a means or mechanism for applying a force or impact stimulus, other types of stimuli (e.g., noise, light, electrical shock, etc.) might alternatively be employed.

Referring now to the drawings, FIG. 1 is a block diagram showing the major elements of a preferred form of the improved device. As there shown, the improved device, generally indicated at 20, broadly includes a hand-held reflex-measuring gun or stimulator 21 arranged to provide a force impact (i.e., stimulus) to a subcutaneous tendon of a patient P, and having a force sensor 22 arranged to measure the time and magnitude of the stimulus force and the patient's physical response thereto. This force sensor is arranged to supply an output signal via line 23 to a computer 24, which is arranged to provide manipulated data to a video display 25, printer 26 and/or a plotter 28, as desired. In the conventional manner, the printer and plotter are adapted to provide hard copy output, described infra, which may be placed in a patient's file. The computer preferably has additional means for storing the data to a hard or floppy disk, or both. Such data may be readily retrieved to the video display, as needed.

In any event, the reflex gun has an associated manually-operated trigger 29 which is arranged to provide an appropriate signal via line 30 through computer 24, and via line 31 to a waveform generator 32. Generator 32 provides an output signal through an amplifier 33 to the reflex gun. The preferred form of the reflex gun has a solenoid-type mechanism for applying an electrically-controlled variable impact force to one end of the force sensor. The time and magnitude of this impact force is sensed, measured and stored. The impact force is transmitted through the force sensor, which is held against the patient's skin with a certain preload force, to a subcutaneous tendon in the patient. The force stimulus delivered to the patient is then transmitted from the tendon along the neuro-muscular conductive nerve path, and causes a contraction of the muscle controlling the affected tendon. This contraction, in turn, causes the patient to involuntarily respond to the stimulus. The time and magnitude of the patient's response is transmitted through the skin to the force sensor, where such values are sensed, measured and stored. Thus, the improved method and apparatus are adapted to sense, measure and monitor certain parameters of the patient's response to the applied stimulus, as well as certain other parameters of the stimulus itself. The parameters include, but are not limited to, the time period between application of the stimulus and the beginning or onset of the patient's response, the magnitude of the impact force, and the force magnitude of the patient's response. This data may be stored in the computer, and manipulated by suitable software to indicate the period of latency, the stimulus-to-response force ratio, and so on. In addition, data from sequential tests may, if desired, be superimposed to allow a ready comparison of such data. This data therefore provides a unique diagnostic tool which allows a physician to apprise objectively and quantitatively the patient's reflex response to the stimulus.

Structure (FIGS. 2–10)

The structure of the preferred form of the improved reflex gun 21 is shown in FIGS. 2–10.

Referring now to FIGS. 2 and 3, the improved reflex gun 21, is shown as broadly including a leftward donut-shaped handle 34 adjacent which a rightward annular trigger 29 is movably mounted. Thus, an operator may grasp the handle with the palm of his hand, and selectively squeeze the trigger with his fingers to initiate the test sequence.

A frame is shown as being fixed to, and as extending rightwardly from, the handle along horizontal longitudinal axis x—x. This frame includes a left member 35, an intermediate member 36, and an arm 38 extending rightwardly therefrom. These three frame members are mounted together by suitable means (not fully shown) to form a rigid frame subassembly.

Left member 35 is shown as being horizontally elongated along axis x—x, and has its left marginal end portion penetrating the donut-shaped handle 34. Member 35 is further depicted has having a rightwardly- and upwardly-facing frusto-conical right end face 39, and has an outwardly-facing horizontal cylindrical surface 40 extending from its left end face (not shown) to the outer margin of its right end face. As shown in FIG. 3, a blind recess extends axially leftwardly into member 35 from the inner margin of its right end face. This recess is bounded by horizontal cylindrical surface 41 extending leftwardly from the inner margin of right end face 39, and by rightwardly-facing circular vertical bottom surface 42.

Intermediate member 36 is shown as being an annular member horizontally elongated along axis x—x, and has its left marginal end portion slidably received in the rightward open mouth of the left member recess. As noted above, the left and intermediate frame members are maintained or held in this relationship by suitable means (not shown). Intermediate frame member 36 is shown as having a horizontal cylindrical outer surface 43 extending between the outer margins of its annular vertical left and right end faces 44,45 respectively. The intermediate frame part also has a stepped axial through-bore, which is sequentially bounded by a horizontal cylindrical surface 46 extending rightwardly from the inner margin of left end face 44, an inwardly- and leftwardly-facing frusto-conical surface 48, and a horizontal cylindrical surface 49 continuing rightwardly therefrom to join the inner margin of right end face 45. As shown in FIG. 3, an annular coil, generally indicated at 50, is arranged in a suitable annular recess provided in intermediate frame member 36 between inner and outer surfaces 46,43. Electrical connector 51 is arranged to provide a signal supplied by amplifier 33 to the coil via suitable conductors (not shown).

A plunger 52 is arranged within the intermediate frame part through-bore for axial sliding movement relative thereto. Plunger 52 is shown as being a solid ferrous member elongated along axis x—x, and has a circular vertical left end face 53, an annular vertical right end face 54, and an outer surface which sequentially includes a horizontal cylindrical surface 55 extending rightwardly from the outer margin of left end face 53, a rightwardly- and outwardly-facing frusto-conical surface 56, a horizontal cylindrical surface 58, a leftward-facing annular vertical surface 59, and a horizontal cylindrical surface 60 continuing rightwardly therefrom to join the outer margin of right end face 54. A cylindrical resilient impact tip 61 is operatively mounted on the right end face of the plunger by means of a recessed fastener (not shown). This impact tip has an annular vertical left end face engaging plunger right end face 54, has an outer cylindrical surface of substantially the same diameter as plunger surface 60, and has an annular vertical right end face arranged in spaced facing relation to the left end face of the force sensor. Thus, the plunger has a cushioned tip arranged to selectively impact against the force sensor.

A C-shaped retaining clip 62 is received in a pair of diametrically-opposed slot-like grooves provided in the left marginal end portion of the plunger. A coil spring 63 surrounds the plunger and is arranged to act between retaining clip 62 and frame surface 44. A resilient O-ring 64 surrounds plunger surface 58, and is arranged to be selectively compressed between frame surface 45 and plunger surface 59. Thus, the plunger is mounted on the frame for axial sliding movement relative thereto along axis x—x. The plunger is biased to move leftwardly relative to the frame by spring 63, with O-ring 64 providing a cushion between frame and plunger surfaces 45,59.

When the operator squeezes the trigger, the waveform generator provides a suitable electrical current pulse via connector 51 to coil 50, to drive the plunger quickly to the right for imparting a sharp, quick impact force against the left end of force sensor 22, as discussed infra. The magnitude of this impact force is substantially proportional to the magnitude of the current supplied to the coil. Moreover, the computer may be operated so as to supply a rapid sequence of current pulses to the coil, for causing the plunger to provide a corresponding plurality of sequential impacts to the force sensor. Thus, the magnitude and timing of the force impact(s) imparted to the force sensor will be a function of the time, spacing, shape and magnitude of the current pulses supplied to the coil.

Frame arm 38 is shown as being a horizontally-elongated bar-like member having its left marginal end portion (not fully shown) suitably secured to the frame intermediate member 36.

A specially-configured block-like member, generally indicated at 65, is mounted on the right marginal end portion of frame arm 38 by means of a plurality of fasteners, one of which is indicated at 66. Member 65 is depicted as being a specially-configured solid member which appears to have a somewhat inverted L-shaped appearance when viewed in side elevation (FIG. 4), and which appears to have a somewhat T-shaped appearance when viewed in end elevation (FIG. 5). Member 65 is shown as having a transversely-thickened upper portion and a transversely-thinner lower portion. As best shown in FIGS. 4 and 5, the member upper portion has planar vertical left and right rectangular end faces 68,69, upper and lower horizontal planar surfaces 70,71, and rectangular vertical side surfaces 72,73, respectively. The upper portion is provided with an axial through-bore bounded by inwardly-facing horizontal cylindrical surface 74 extending between end faces 68,69. A pair of slot-like recesses communicate side surfaces 72,73 with through-bore 74, and extend leftwardly into the member upper portion from its right end face 69. Each of these slot-like recesses is shown as including a pair of upper and lower horizontal planar surfaces 75,76 extending leftwardly from right end face 69, and an arcuate concave surface 78 joining their left marginal end portions. The member upper portion is further provided with a pair of blind tapped holes (not shown) extending downwardly into the member from its upper surface 70 to accommodate fasteners 66. The frame lower surface 71 is somewhat U-shaped.

The member lower portion is shown as being another rectangular block-like member formed integrally with the member upper portion, and extending vertically downwardly therefrom. The lower portion has a planar vertical left end face 79 extending downwardly from upper portion left end face 68 and being substantially flush therewith, a planar vertical right end face 80, a planar horizontal surface 81, and a pair of planar vertical side surfaces 82,83, respectively. The member lower portion is provided with a tapped horizontal through-hole 84 which extends between end faces 79,80 as to be substantially parallel to axis x—x. Another tapped vertical hole 85 extends upwardly from member lower face 81 to intersect horizontal hole 84. The member may be formed integrally, as previously noted, or may be formed of two separate members, subsequently assembled together, as desired.

Adverting now FIGS. 2, 3, 6 and 7, a trough-like slide member, generally indicated at 86, is mounted on the lower portion of member 65 for horizontal sliding movement relative thereto. As best shown in FIGS. 6 and 7, slide member 86 is horizontally-elongated, and is depicted as having planar vertical left and fight end faces 88,89, planar horizontal upper and lower surfaces 90,91, and planar vertical side surfaces 92,93, respectively. As previously noted, slide member 86 is in the form of a horizontally-shaped elongated rectangular trough. The inner trough portion is bounded by left and right planar vertical surfaces 94,95, a horizontal planar bottom surface 96, and by inwardly-facing side surfaces 98,99, respectively. The left wall of slide member 86 is provided with a central horizontal through-opening bounded by inwardly-facing horizontal cylindrical surface 100 extending between surfaces 88,94. The right wall of the slide member is provided with a stepped through-opening which is sequentially bounded by an inwardly-facing horizontal cylindrical surface 101 extending rightwardly from trough surface 95, a rightwardly-facing annular vertical surface 102, and a horizontal cylindrical surface 103 continuing rightwardly therefrom to join right end face 89. These two through-openings are co-axial. A corner groove extends into the slide member from the intersection of lower face 91 and right end face 89. This corner groove is bounded by a rightwardly-facing planar vertical surface 104 extending upwardly from lower surface 91 to intersect through-bore surface 103, and a downwardly-facing horizontal planar surface 105 extending rightwardly therefrom to join right end face 89. A pair of tapped blind holes, severally indicated at 106 extend leftwardly into the slide member from corner groove surface 104. A slot-like through opening communicates trough bottom 96 with lower surface 91. More particularly, this opening is bounded by facing left and right planar vertical surfaces 108,109, and by facing planar vertical side surfaces 110, 111, respectively.

As best shown in FIG. 3, the lower portion of member 65 is arranged within the trough of slide member 86, with member downwardly-facing surface 71 slidably engaging slide member upper surface 90. A horizontally-elongated externally threaded shaft 112 penetrates the through-bore provided through the left wall of the slide member, has an intermediate portion threadedly engaging tapped block member hole 84, and has its right marginal end portion rotatably received in right through-bore 101. Rod 112 may be held in this operative position by means of a set screw 113 acting through a washer 114 and matingly received in a tapped blind hole 115 extending into the shaft from its annular vertical right end face. A knob 116 is mounted fast to the left marginal end of threaded shaft 112. Thus, this knob may be grasped and selectively rotated to translate the slide member horizontally relative to the tube member 65.

Another threaded shaft 118 is matingly received in tapped member hole 85. The shaft 118 has a knob 119 on its lower marginal end portion. Thus, this knob may be selectively tightened against slide member lower surface 91 to releasably hold the slide in any desired horizontal position relative to the member.

A vertically-elongated curved arcuate member, generally indicated at 120, is mounted in the corner recess of the slide, and extends downwardly therefrom. Member 120 has a somewhat C-shaped horizontal cross-section, and is provided with a central through-opening bounded by arcuate upper and lower surfaces 121,122, and vertical side surfaces, one of which is indicated at 123. Member 120 has planar horizontal upper and lower end faces 124,125, a rightwardly-facing concave cylindrically segmented surface 126, and a leftwardly-facing convex cylindrically segmented surface 128. Member 120 provides a support which is adapted to bear against a portion of a patient's skin when the device is in use.

Referring now to FIGS. 8–10, the force sensor 22 is shown as including (from left-to-right): an end cap 129, a body member 130, a spacer 131, a transducer 132, a head 133, a tip 134, and a bolt 135. An amplifier-connector 136 is shown as being radially aligned with an opening provided in member 130.

End cap 129 is bolt-like member provided with a radially-enlarged hexagonal head 138, and with a horizontally-extending externally-threaded stem 139.

Body member 130 is shown as being a horizontally-elongated specially-configured member having annular vertical left and right end faces 140,141, and a stepped outer surface including horizontal cylindrical surface 142 extending rightwardly from the outer margin of left end face 140, a leftwardly-facing annular vertical surface 143, and a horizontal cylindrical surface 144 continuing rightwardly therefrom to join the outer margin of right end face 141. A tapped blind hole, indicated at 145, extends axially into the body member from its left end face 140. A stepped recess extends leftwardly into body member 142 from its right end face. More particularly, this recess is bounded by an inwardly-facing horizontal cylindrical surface 146 extending leftwardly from right end face 141, a rightwardly-facing annular vertical surface 148, and a blind hole 149 extending further axially into the body member from surface 148.

As best shown in FIG. 3, a slot is milled into the body member from outer surface 142. More particularly, and as best shown in FIG. 9, this slot is bounded by facing vertical left and right chordal surfaces 150,151, and by a planar horizontal bottom surface 152 which appears to be rectangular when viewed in elevation (FIG. 3). A tapped vertical hole 153 extends downwardly into the body member from slot bottom surface 152 to intersect hole 149. Amplifier-connector 136 is shown as being arranged to be matingly received in this hole for providing a means by which the output signal of the transducer may be supplied to the computer.

Spacer 131 is shown as being a horizontally-elongated thin-walled cylindrical member, preferably formed of delrin or some other suitable or electrical non-conductive plastic material. More particular, spacer 131 is shown as having annular vertical left and right end faces 154,155, and inner and outer horizontal cylindrical surfaces 156,158, respectively. Spacer 131 is arranged to be received within the relatively large diameter open mouth of the rightward recess provided in the body member, such that spacer left end face 154 will abuttingly engage recess bottom surface 148, with spacer outer surface 158 arranged to face recess surface 146.

The transducer 132 is shown as including a pair of X-cut piezoelectric crystals, severally indicated at 159. These two crystals are in the form of vertically-disposed circular disks, and have an electrode 160 sandwiched between their facing surfaces. Transducer 132 is arranged to be received within spacer 131, such that an annular portion of the left face of the left crystal is arranged to bear against a facing portion of body member recess surface 148.

Head member 133 is shown as being a specially-configured solid member having a circular vertical left end face 161, an annular vertical right end face 162, and an outer surface sequentially including a horizontal cylindrical surface 163 extending rightwardly from the outer margin of left end face 161, a rightwardly- and outwardly-facing frustoconical surface 164, a horizontal cylindrical surface 165, a leftwardly-facing annular vertical surface 166, a horizontal cylindrical surface 168, a rightward-facing annular vertical surface 169, and a horizontal cylindrical surface 170 continuing rightwardly therefrom to join the outer margin of right end face 162. Surfaces 166,168,169 define a radially-extending annular flange that extends circumferentially about the head member. A tapped blind hole 171 extends axially leftwardly into the head member from its right end face 162. The left marginal end portion of the head member is adapted to be slidably received within spacer 131 such that head member left end face 161 is arranged to bear against the right face of the rightward crystal, as shown in FIG. 9. In this position, flange surface 166 is arranged to abut spacer right end face 155 and body member right end face 141. The head member is adapted to be secured in this position by means of a peripheral weldment, indicated at 172 in FIG. 9.

The impact tip is shown as being a specially-configured resilient member having an annular vertical left end face 173, a vertically-elongated concave annular vertical right end face 174, and a horizontal cylindrical outer surface 175. Tip 134 is provided with a stepped axial through-bore, which sequentially includes a horizontal cylindrical surface 176 extending rightwardly from left end face 173, a rightwardly-facing annular vertical surface 178, and a horizontal cylindrical surface 179 continuing rightwardly therefrom to join concave right end face 174. As shown in FIG. 9, the left end face 173 of the impact tip is arranged to bear against head member right end face 162. Bolt 135 is adapted to penetrate impact tip hole 176 and to be matingly received in head member threaded recess tapped blind hole 171.

The force sensor is assembled as shown in FIG. 9. The relatively thin flange on the head member mounts the head member for limited axial movement toward and away from body member surface 148. An electrical conductor 180 joins the electrode 160 between the two piezoelectric crystals with amplifier-connector 136. The assembled force member is slidably arranged within the through-bore 74 of member 65. A pair of O-rings, severally indicated at 181 surround the left marginal end portion of the sensor body member and are arranged between the exposed portion of the end cap head 138 and member left end face 68. Another O-ring, again indicated at 181 surrounds sensor body member surface 142 and is operatively arranged between member right end face 69 and force sensor surface 143. These several O-rings are so positioned to cushion acceleration and deceleration of force sensor 22 relative to the block-like body member 65.

Operation

The structure heretofore described is assembled as shown. Knob 119 may be selectively rotated to permit slide member 86 to be moved horizontally relative to the block-like member 65 by means of rotation of knob 116. The effect of this is to selectively position support member 120 relative to the patient to adjust the preload force by which the impact tip right face 174 will engage the patient. In other words, if the slide member is moved leftwardly from the position shown in FIGS. 2 and 3, the force sensor impact tip will press against the patient's skin with greater force when the improved gun is pushed against the patient's skin. Conversely, if support member 120 is moved to a position rightwardly of that shown in FIGS. 2 and 3, the preload force will be reduced. For most patients, the preload force may be a relatively small, perhaps on the order of from about 1–3 lbs [0.45–1.36 kg]. After adjusting the preload force, the operator simply picks up the gun by grasping handle 34, and presses it against the patient's skin so that the rightward impact tip of the force sensor is aligned with a tendon to be tested. The operator then pushes the device against the patient's skin, with support member 120 bearing against the patient's skin. As previously noted, the device has been previously adjusted to cause the force sensor to exert a preload force on the order of 1–3 lbs. on the patient's skin, in order to bear against the subcutaneous tendon. This preload force is transmitted through the head member to the transducer, and is sensed by the computer.

Once so positioned, the operator then squeezes trigger 29 with his fingers. This causes the computer to supply an initiating signal to waveform generator which, in turn, supplies a current pulse of desired shape, duration, and magnitude to coil 50. When the coil is energized, plunger 52 is driven quickly to the right, impacting upon the left end face of the force sensor. This, in turn, drives the force sensor rightwardly to apply an impact force to the tendon. This force is in turn transmitted along the neuro-muscular conducive path, and causes an involuntary reaction in the muscles controlling the tendon. Such reaction force of the tendon is transmitted back through the skin to the force sensor, and its time, duration and magnitude are again sensed by the transducer. Such data with respect to the patient's reflex is then transmitted to the computer, where it is stored. This data may be then displayed on the display, the printer and/or the plotter, as desired.

Figure 11:
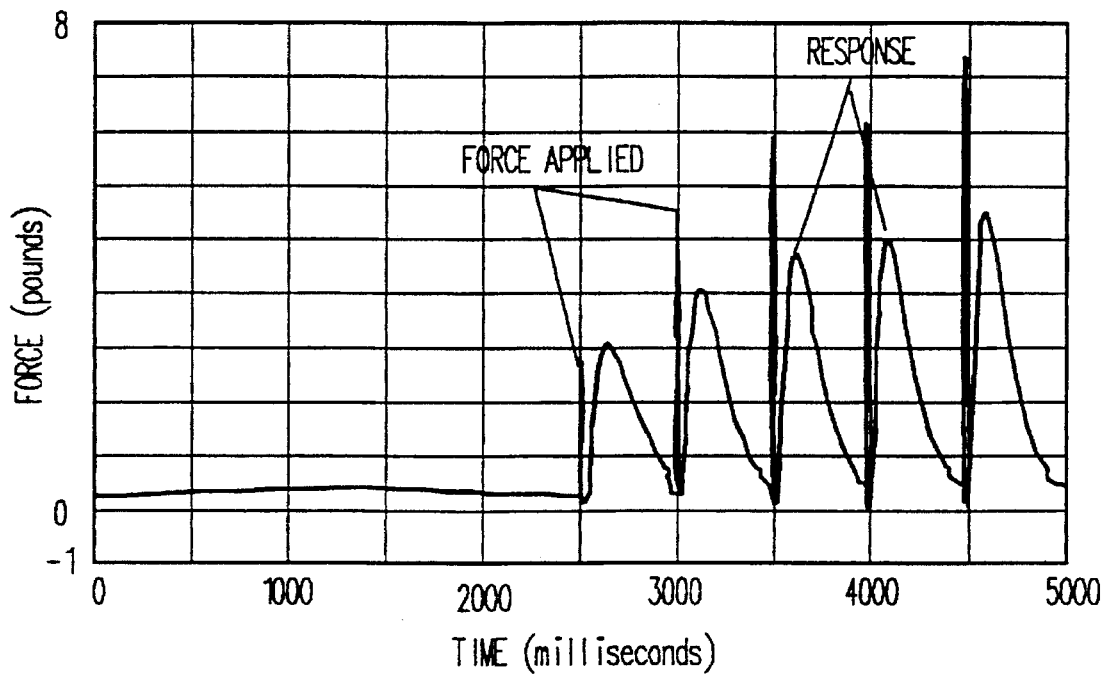
FIG. 11 is a representative plot of force (ordinate) vs. time (abscissa) showing the five sequentially-applied stimuli of progressively-increasing force amplitude and the patient's responses thereto.
Figure 12:
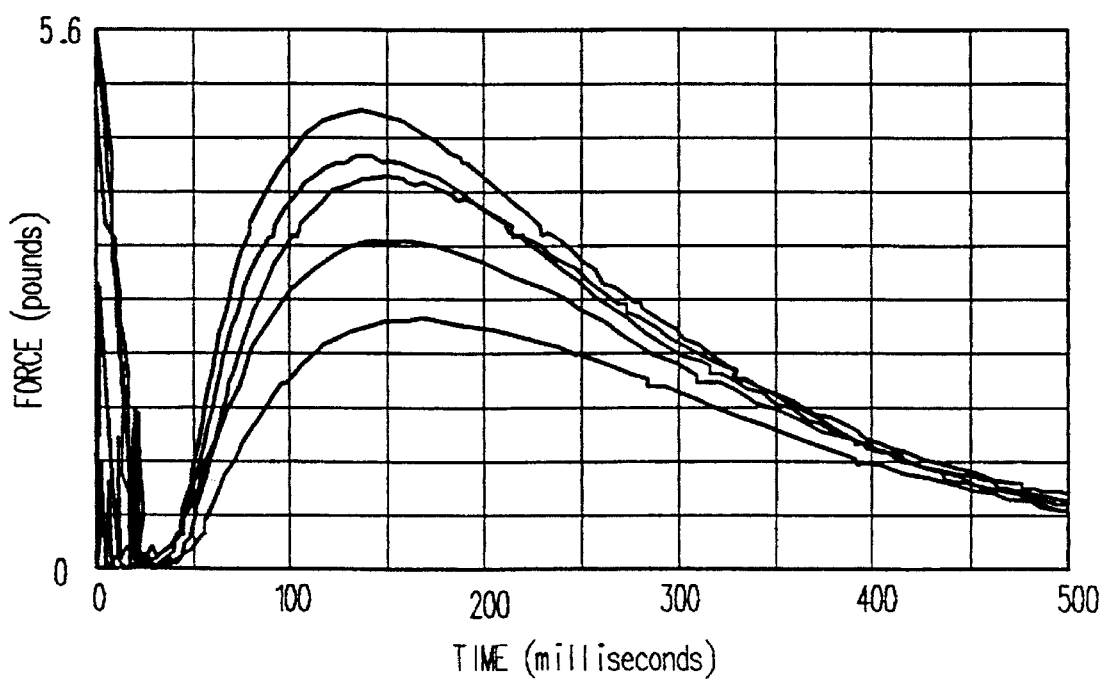
FIG. 12 is a plot of force (ordinate) vs. time (abscissa) showing the five stimuli and responses as being superimposed.
Figure 13:
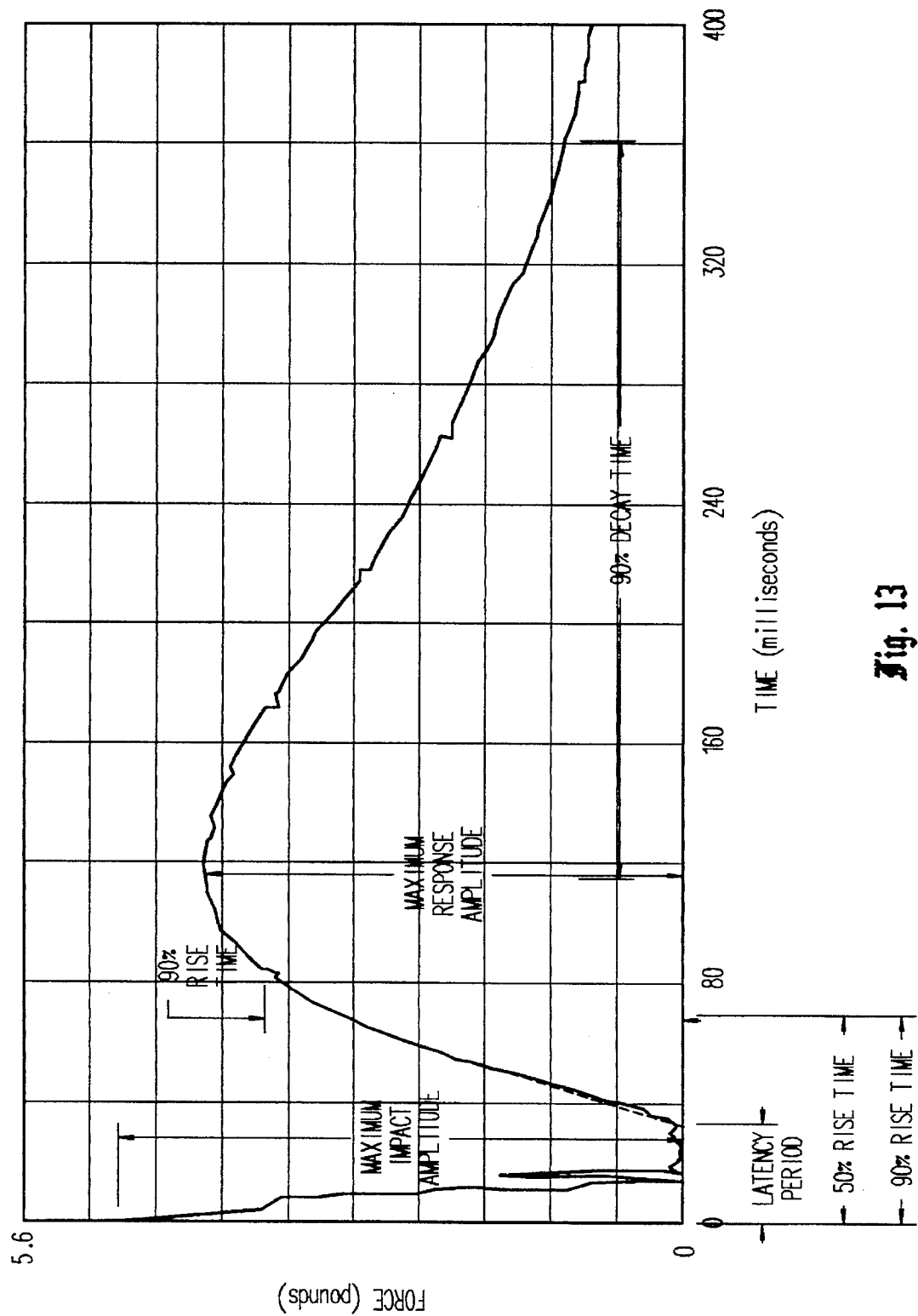
FIG. 13 is a plot of force (ordinate) vs. time (abscissa) of one of the stimuli and responses shown in FIG. 11, and indicating the period of latency between the peak of the stimulus and the onset of the patient's response, and also showing other parameters of the patient's response.

FIGS. 11–13 illustrate representative data from the test on a patient's quadricep tendon. FIG. 11 is a plot of force (ordinate) vs. time (abscissa) and shows the application of five sequential impacts, spaced nominally about 500 milliseconds apart to the tendon. This figure also illustrates the patient's response to such stimuli. To obtain this curve, the computer was programmed to cause the waveform generator to provide five sequential current pulses, of progressively-increasing magnitude, to the reflex gun, for producing the sequential impacts to the patient's tendon. The patient's response is illustrated between sequential pulses. This test was conducted in order to ensure that at least one of the curves was between the minimum and maximum threshold limits of the device's sensitivity. For example, if the device is held too lightly against the patient's skin, or if the force stimulus is too small, this may not produce a measurable response. On the other hand, there may be a maximum stimulus force above which no greater response is generated. In any event, the curves depicted in FIG. 1 were obtained to provide the patient's responses to five sequential pulses of different magnitude.

FIG. 12 shows the result of some mathematical manipulation of the initial data shown in FIG. 11. This is provided by suitable software to the computer. FIG. 12 is a curve of force (ordinate) vs. time (abscissa), but shows the five stimuli and responses as being superimposed on one another, and further displays time in a different scale. In FIG. 12, the maximum impact force occurs at time t=0 (i.e., zero milliseconds). FIG. 12 illustrates a family of curves, of generally similar shape, showing the patient's responses to such progressively-increasing force stimuli.

FIG. 13 is an enlarged view of only one of the curves shown in FIG. 12. FIG. 13 again illustrates force (ordinate) vs. time (abscissa). FIG. 13 is provided to isolate the data of only one stimulus and its response, and shows certain diagnostic parameters that may be gathered therefrom. First, the magnitude of the impact force may be determined. Secondly, the maximum magnitude of the patient's response may be determined. The latency period (i.e., the time period between the maximum stimulus and the onset of the patient's response) is also shown. Certain additional factors, such as half rise time, 90% rise time, half decay time, 90% decay time, and the like, may also be determined. These latter factors reflect the particular shape of the curve. From this data, the latency period, the stimulus-to-response force ratio, and the like, may be determined.

As previously indicated, this data may be saved to either a hard disk or to hard copy. Thus, the physician may take a test at one time, and save the results. Thereafter, the physician may take a second test on the same tendon at a later time, and may then compare the results of the two tests. For example, a decrease in the latency period from one test to the other might well show an improvement in the patient's initial condition. Similarly, variances in the stimulus-to-response force ratio may likewise indicate the patient's condition or changes in the same. Thus, much and different quantitative data may be obtained by use of the improved device.

Modifications

The present invention contemplates that many changes and modifications may be made. For example, the illustrated form of the reflex gun is shown as having a solenoid-type device for providing a force impact, or multiple force impacts, of known force. This feature could be eliminated, and the physician could simply tap the left end of the force sensor. While such manually-applied stimulus will indeed be measured by the force sensor, the feature of the solenoid offers the advantages of being able to provide forces of controllable magnitude. Moreover, the solenoid also allows the physician to apply sequential stimuli, as desired. In any event, the solenoid force generator may be eliminated, if desired. Other types of stimuli (e.g., light, noise, electrical shock, etc.) might be used.

Force or displacement transducers other than piezoelectric crystals may also be employed. Similarly, the particular means or mechanism for adjusting the preload applied to the patient may also be changed. In a crude form, the physician may simply grasp the force sensor, and, holding it loosely against the skin, simply tap the left end thereof to apply the stimulus to the tendon, and to measure its response. However, this embodiment, while functionally operational, is believed to be less desirable than the mechanical embodiment shown. Other mechanisms, such as an instrumental chair or a temporary splint attached to the subject being treated, may be employed to increase the mechanical grounding of the device.

Therefore, while a preferred embodiment of the improved method and apparatus has been shown and described, and several modifications thereof discussed, persons skilled in this art will readily appreciate that various additional changes and modifications may be made without departing from the spirit of the invention, as defined and differentiated by the following claims.

We claim:

1. A reflex measuring device for measuring certain parameters of a patient's physical response to application of an external stimulus, comprising:

stimulus means for selectively applying a stimulus to the patient; and sensor means for sensing and measuring the period of latency between the application of said stimulus and the beginning of the patient's physical response thereto, said sensor means having a member and a head mounted for movement toward and away from one another and having a transducer operatively arranged between said member and head and arranged to provide an output signal as a function of the relative positions of said member and head, said head having a surface adapted to continuously bear against a portion of the patient's skin between the application of the stimulus and the end of the measurement of the response;

whereby said transducer output signal will be a function of the patient's response to said stimulus.

2. A reflex measuring device as set forth in claim 1 wherein said transducer is arranged to sense and measure the force transmitted from said heat to said member.

3. The improvement as set forth in claim 2 wherein said transducer includes at least one piezoelectric crystal.

4. A reflex measuring device as set forth in claim 1 wherein said surface is arranged to bear against a tendon through the patient's skin.

5. A reflex measuring device as set forth in claim 4 wherein said stimulus means is arranged to supply a force stimulus to said tendon.

6. A reflex measuring device as set forth in claim 5 wherein said force stimulus is applied to said tendon through said sensor.

7. A reflex measuring device as set forth in claim 1 and further comprising a frame adapted to engage the patient's body, and wherein a force sensor is movably mounted on said frame.

8. A reflex measuring device as set forth in claim 7 and further comprising electromagnetic means mounted on said frame for selectively applying an impact force to said force sensor.

9. A reflex measuring device as set forth in claim 8 wherein said electromagnetic means includes a coil mounted on said frame, and a plunger mounted for movement toward said force sensor when said coil is energized.

10. A reflex measuring device as set forth in claim 1 wherein one of said certain parameters includes the period of latency between the application of said stimulus and the beginning of said response.

11. A reflex measuring device as set forth in claim 1 wherein one of said certain parameters includes the amplitude of said response.

12. A reflex measuring device as set forth in claim 1 wherein said sensor means includes means for recording and displaying data with respect to said certain parameters.

13. A reflex measuring device as set forth in claim 12 wherein said parameters are displayed on a video screen.

14. A reflex measuring device as set forth in claim 12 wherein said parameters are displayed on a plotter.

15. A reflex measuring device as set forth in claim 12 wherein said parameters are displayed on a printer.

* * * * *